United States Patent [19]

Yoon

[11] Patent Number: 5,336,176

[45] Date of Patent: Aug. 9, 1994

[54] AUTOMATIC RETRACTABLE SAFETY PENETRATING INSTRUMENT

[76] Inventor: InBae Yoon, 2101 Highland Ridge Dr., Phoenix, Md. 21131

[21] Appl. No.: 868,578

[22] Filed: Apr. 15, 1992

Related U.S. Application Data

[63] Continuation-in-part of Ser. No. 805,506, Dec. 6, 1991, abandoned.

[51] Int. Cl.$^5$ ............................................. A61M 5/178
[52] U.S. Cl. ................................. 604/51; 604/164; 604/174; 604/272; 606/185
[58] Field of Search .................. 604/51, 164-169, 604/174, 175, 264, 272, 273, 274; 606/184, 185

[56] References Cited

U.S. PATENT DOCUMENTS

| | | |
|---|---|---|
| Re. 32,922 | 5/1989 | Levin et al. . |
| 1,527,291 | 2/1925 | Zorraquin . |
| 2,496,111 | 1/1950 | Turkel . |
| 2,623,521 | 12/1952 | Shaw . |
| 2,630,803 | 3/1953 | Baran .................... 604/158 |
| 3,680,562 | 8/1972 | Wittes et al. ............ 604/51 |
| 4,254,762 | 3/1981 | Yoon . |
| 4,345,589 | 8/1982 | Hiltebrandt . |
| 4,442,836 | 4/1984 | Meinecke et al. . |
| 4,488,545 | 12/1984 | Shen . |
| 4,503,856 | 3/1985 | Cornell et al. . |
| 4,535,773 | 8/1985 | Yoon ....................... 604/51 |
| 4,559,041 | 12/1985 | Razi ........................ 604/157 |
| 4,601,710 | 7/1986 | Moll ........................ 604/165 |
| 4,627,841 | 12/1986 | Dorr ........................ 604/158 |
| 4,654,030 | 3/1987 | Moll et al. .............. 604/165 |
| 4,670,008 | 6/1987 | Von Albertini ........ 604/165 |
| 4,677,979 | 7/1987 | Burns . |
| 4,747,831 | 5/1988 | Kulli ....................... 604/110 |
| 4,817,603 | 4/1989 | Turner et al. . |
| 4,820,275 | 4/1989 | Haber et al. ........... 604/198 |
| 4,869,717 | 9/1989 | Adair ...................... 604/51 |
| 4,889,117 | 12/1989 | Stevens .................. 606/189 |
| 4,900,307 | 2/1990 | Kulli ....................... 604/110 |
| 4,902,280 | 2/1990 | Lander .................... 604/165 |

(List continued on next page.)

FOREIGN PATENT DOCUMENTS 2544262 4/1977 Fed. Rep. of Germany .
1435246 11/1988 U.S.S.R. .

*Primary Examiner*—Randall L. Green
*Assistant Examiner*—Mary Beth Jones

[57] ABSTRACT

A retractable safety penetrating instrument includes a cannula, a penetrating member disposed within the cannula and a hub mounting proximal ends of the penetrating member and the cannula. The penetrating member is movable to an operative state to penetrate tissue wherein a sharp tip of the penetrating member extends beyond a distal end of the cannula, and is arranged to be moved to a retracted position with the sharp tip of the penetrating member disposed within the cannula in a safe, protected position upon penetrating through the tissue. The penetrating member is selectively movable to various extended positions following retraction such that the sharp tip of the penetrating member can be positioned in an anatomical cavity to perform various medical procedures. The cannula can include various distensible, expandable or shape changing devices automatically positioned in response to retraction of the penetrating member to stabilize or hold the instrument within an anatomical cavity. A method of performing surgical procedures includes the steps of automatically retracting a sharp tip of the penetrating member within a cannula, moving the penetrating member distally to cause the sharp tip to protrude beyond a distal end of the cannula and performing a procedural step with the penetrating member.

22 Claims, 4 Drawing Sheets

U.S. PATENT DOCUMENTS

| | | | |
|---|---|---|---|
| 4,906,236 | 3/1990 | Alberts et al. | 604/198 |
| 4,931,042 | 6/1990 | Holmes et al. | 604/164 |
| 4,943,280 | 7/1990 | Lander | 604/169 |
| 4,946,446 | 8/1990 | Vadher | 604/198 |
| 4,955,870 | 9/1990 | Ridderheim et al. | 604/195 |
| 4,966,593 | 10/1990 | Lennox | 604/198 |
| 4,973,316 | 11/1990 | Dysarz | 604/195 |
| 4,986,814 | 1/1991 | Burney et al. | 604/164 |
| 4,994,042 | 2/1991 | Vadher | 604/165 |
| 4,994,068 | 2/1991 | Hufnagle | 606/181 |
| 5,024,665 | 6/1991 | Kaufman | 604/179 |
| 5,026,388 | 6/1991 | Ingaiz | 606/182 |
| 5,030,206 | 7/1991 | Lander | 604/164 |
| 5,053,016 | 10/1991 | Lander | 604/169 |
| 5,061,251 | 10/1991 | Juhasz | 604/198 |
| 5,066,288 | 11/1991 | Deniega et al. | 604/274 |
| 5,104,382 | 4/1992 | Brinkerhoff et al. | 604/165 |
| 5,104,383 | 4/1992 | Shichman | 604/167 |
| 5,114,407 | 5/1992 | Burbank | 604/164 |
| 5,116,353 | 5/1992 | Green | 604/160 |
| 5,127,909 | 7/1992 | Shichman | 604/165 |
| 5,152,754 | 10/1992 | Plyley et al. | 604/164 |
| 5,158,552 | 10/1992 | Borgia et al. | 604/165 |
| 5,192,298 | 3/1993 | Smith et al. | 606/205 |
| 5,226,426 | 7/1993 | Yoon | 604/169 X |

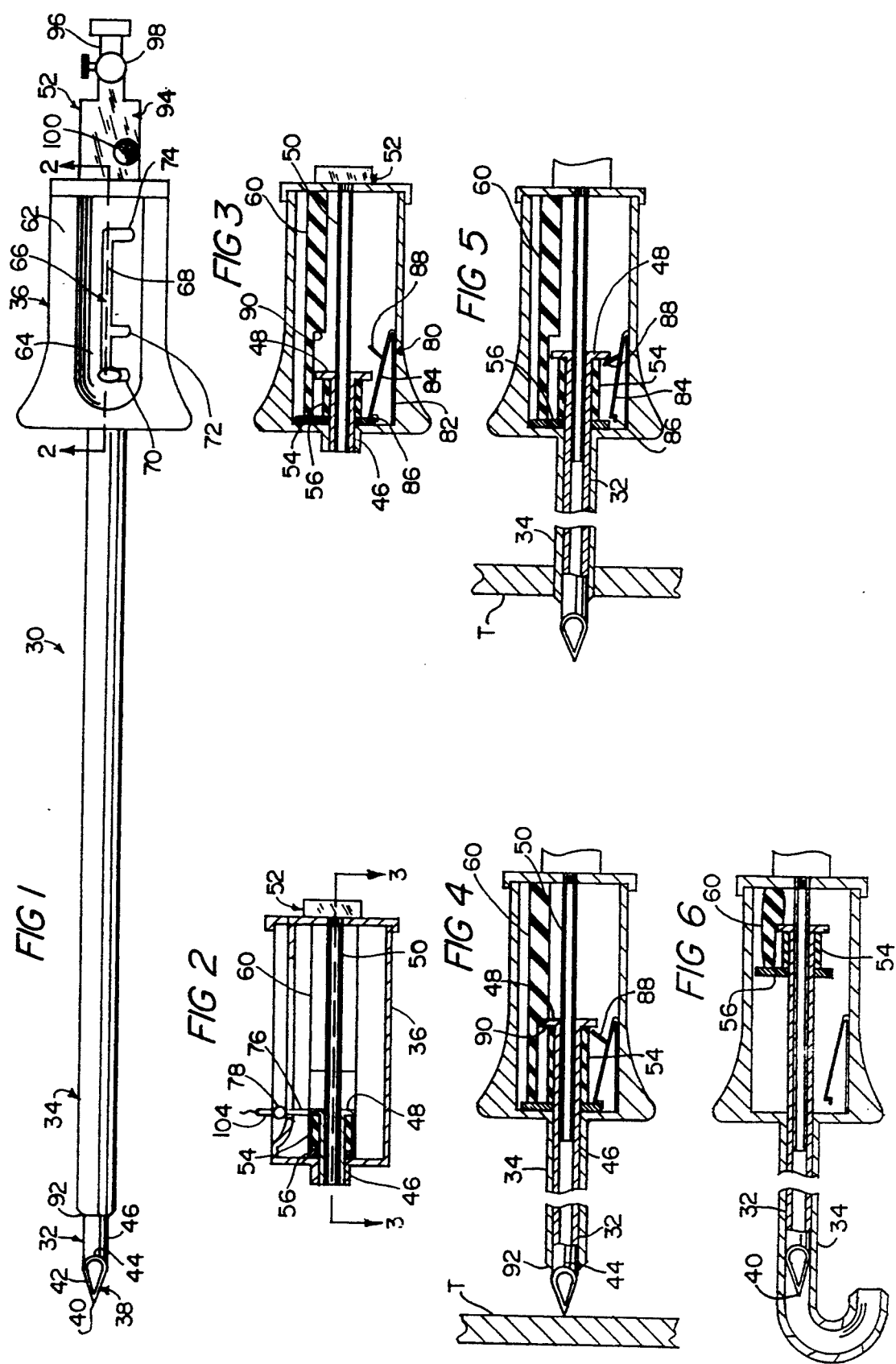

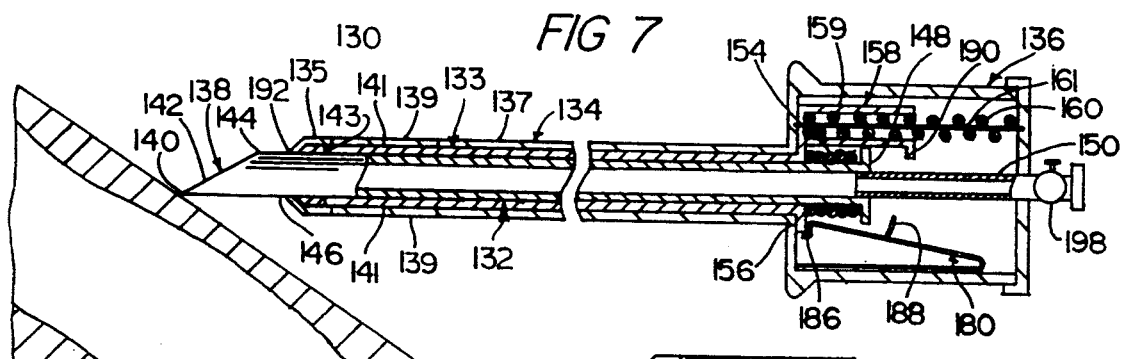
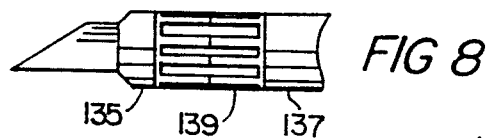
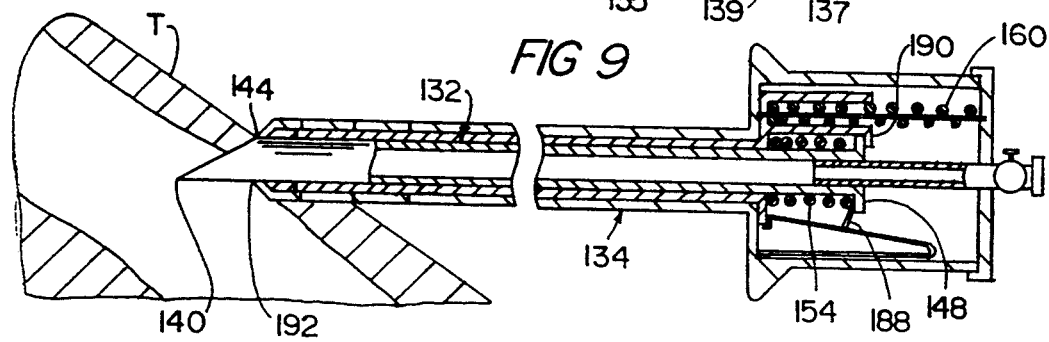
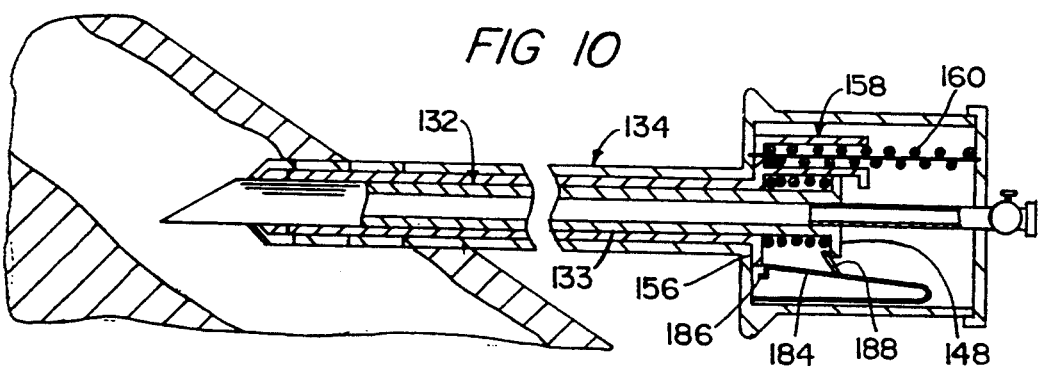
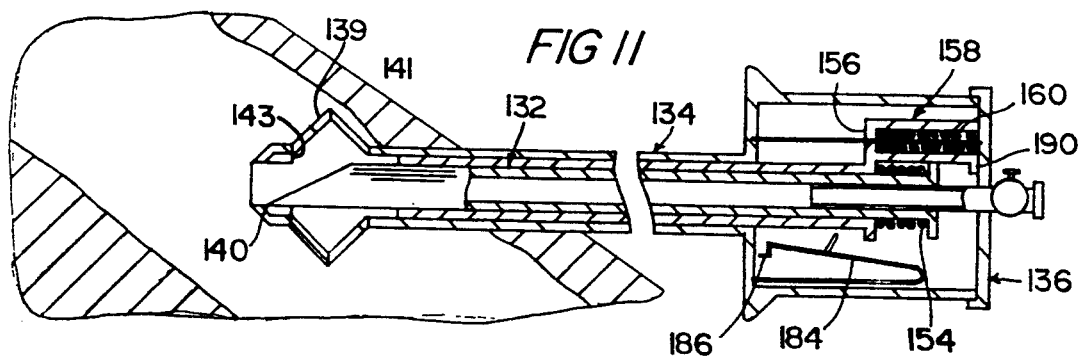

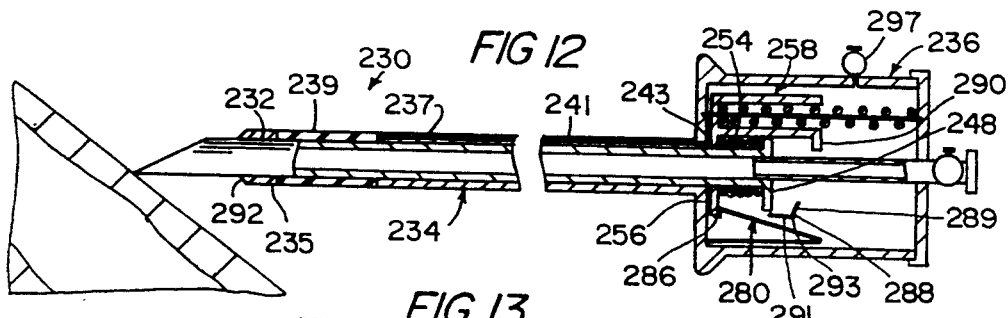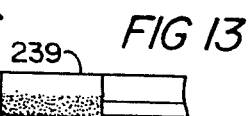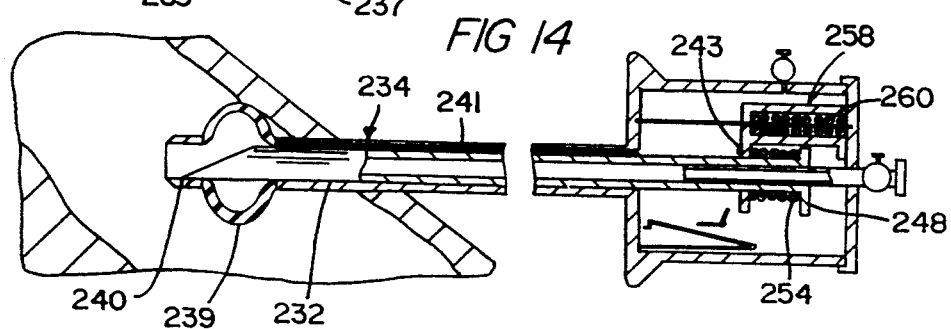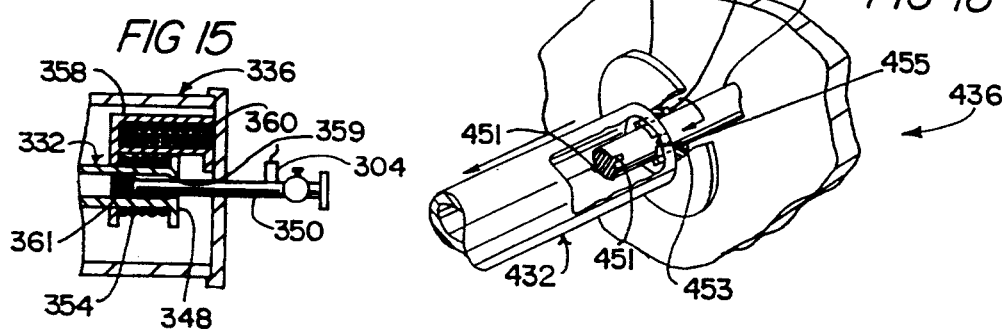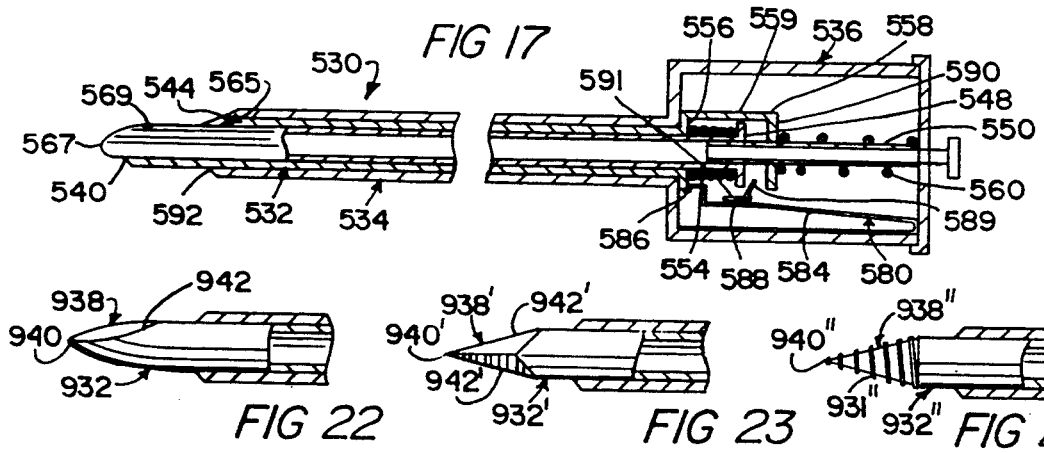

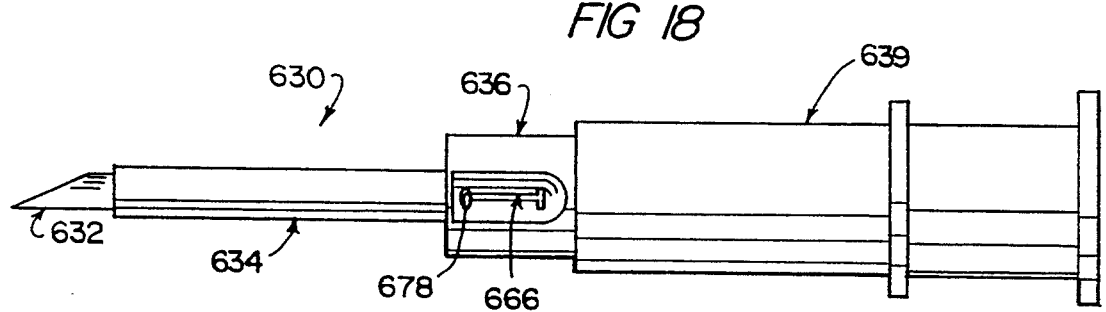
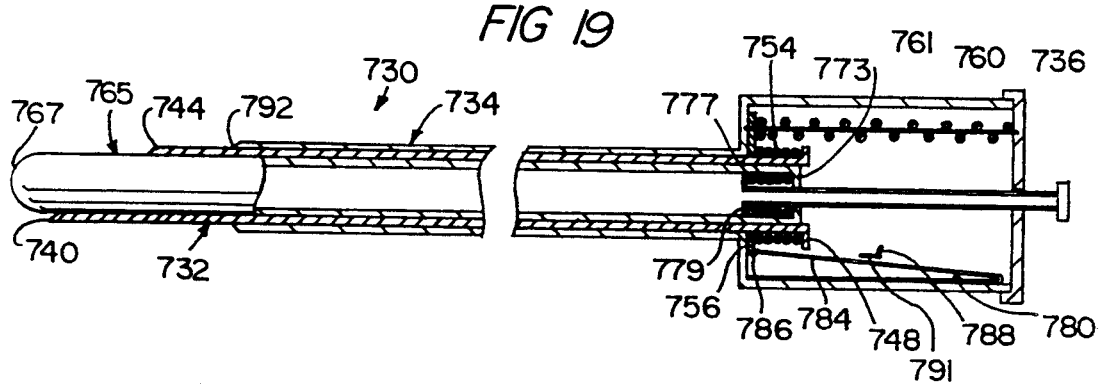
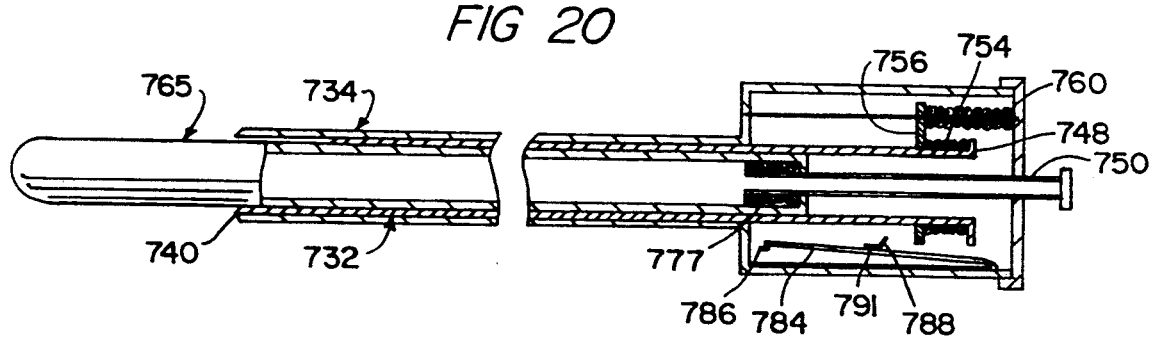
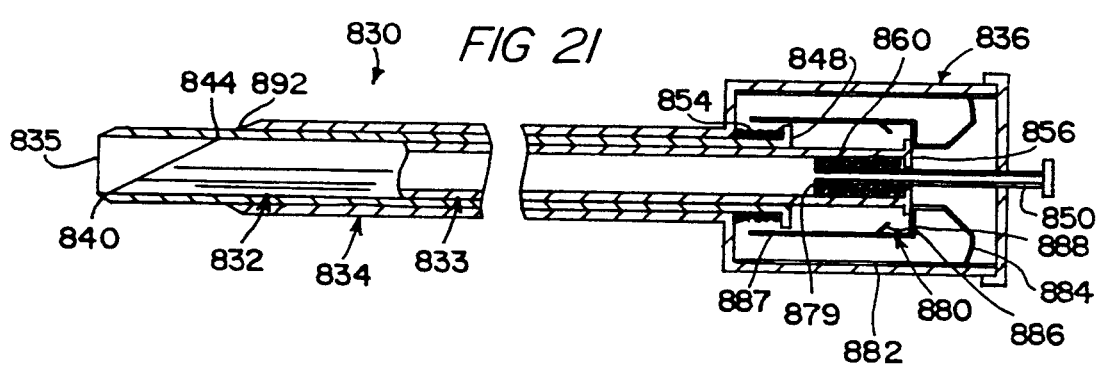

AUTOMATIC RETRACTABLE SAFETY PENETRATING INSTRUMENT

CROSS REFERENCE TO RELATED APPLICATIONS

This application is a continuation-in-part of pending patent application Ser. No. 07/805,506, filed Dec. 6, 1991, now abandoned. The specifications of pending patent applications Ser. No. 07/800,507, filed Nov. 27, 1991, Ser. No. 07/805,506 and Ser. No. 07/808,325, filed Dec. 16, 1991, and Ser. No. 07/848,838, filed Mar. 10, 1992, all naming InBae Yoon as inventor are incorporated herein by reference.

BACKGROUND OF THE INVENTION

1. Field of the Invention

The present invention pertains to safety penetrating instruments and, more particularly, to automatic safety penetrating instruments having outer sleeves for introduction into anatomical cavities and penetrating members within the outer sleeves with sharp tips for penetrating cavity walls.

2. discussion of the Prior Art

Penetrating instruments are widely used in medical procedures to gain access to anatomical cavities ranging in size from the abdomen to small blood vessels, such as veins and arteries, epidural, plueral and subarachnoid spaces, heart ventricle and spinal and synovial cavities, with access being established via an outer sleeve or cannula positioned during penetration into the cavity with the penetrating instrument. Such penetrating instruments include a penetrating member having a sharp tip or point to pierce or penetrate the tissue forming the cavity wall, and the force required to penetrate the cavity wall is dependent upon the type and thickness of the tissue of the wall. Once the wall is penetrated, it is desirable to prevent the sharp tip of the penetrating member from inadvertent contact with or injury to tissue or organ structures in or forming the cavity, and a particular problem exists where substantial force is required to penetrate the cavity wall or the cavity is very small in that, once penetration is achieved, the lack of tissue resistance can result in the sharp tip traveling too far into the cavity and injuring adjacent tissue or organ structures.

Safety penetrating instruments including a safety probe biased to extend beyond the sharp tip of a penetrating member have become widely accepted for use in penetrating anatomical cavities. For example, the Verres needle, commonly used to create a pneumoperitoneum, has a spring-loaded inner member disposed within a tubular needle. U.S. Pat. No. 1,527,291 to Zorraquin, No. 2,623,521 to Shaw and No. 2,630,803 to Baran are exemplary of safety penetrating instruments with a spring-loaded inner member disposed in a needle, while U.S. Pat. No. 4,254,762 to Yoon shows an endoscope spring-biased in a hollow needle. German Offengulaschrift 2,544,262 discloses an intrauterine catheter including a tube having a distal sharp point, a spring-biased blunt member in the tube distal end and a hose or catheter slidable over the tube.

Safety trocars having a spring-biased protective shield disposed between an outer sleeve and an inner trocar are marketed by Ethicon, Inc. as the Endopath and by United States Surgical Corp. as the Surgiport. U.S. Pat. No. 4,535,773 to Yoon, No. 4,601,710 to Moll and No. 4,654,030 to Moll et al are illustrative of such safety trocars. A trocar disposed within a portal sleeve and retractable within the sleeve in response to an electrical signal generated when force from tissue contact is removed from the sharp tip of the trocar is set forth in U.S. Pat. No. 4,535,773 to Yoon.

One of the limitations of many prior art safety penetrating instruments is that the safety probes can produce an irregular surface or profile with the sharp tips of the penetrating members during penetration of tissue resulting in increased resistance during penetration of a cavity wall, trauma and damage to tissue and possible jamming and trapping of tissue. Another limitation of many prior art safety penetrating instruments is that very small or narrow anatomical cavities cannot be penetrated without protrusion of the safety probes or shields from the sharp tips of the penetrating members. A further limitation of many prior art penetrating instruments is that the penetrating members cannot be automatically retracted, with or without the safety probes or shields within the outer sleeves upon penetration into an anatomical cavity. Many prior art penetrating instruments are also limited in that the penetrating members cannot be automatically retracted to safe, protected positions wherein the sharp tips of the penetrating members are disposed within the instruments upon penetration into anatomical cavities and thereafter selectively moved to various extended positions with the sharp tips protruding into the cavities for performing various surgical procedures. Many prior art safety penetrating instruments are also limited in that the instruments cannot be automatically held, anchored or stabilized within the anatomical cavities upon penetration therein or selectively anchored where automatic stabilization is not desired.

SUMMARY OF THE INVENTION

Accordingly, it is a primary object of the present invention to overcome the above-mentioned disadvantages of prior art safety penetrating instruments.

Another object of the present invention is to automatically retract a penetrating member of a safety penetrating instrument to a safe, protected position within the instrument upon a distal end of an outer sleeve entering an anatomical cavity and to allow the penetrating member to be selectively moved to an extended position beyond the distal end of the outer sleeve for performing various surgical procedures with the penetrating member within the anatomical cavity.

A further object of the present invention is to arrange a penetrating member in a safety penetrating instrument such that the distance that the penetrating member can be moved distally to protrude into an anatomical cavity following retraction of the penetrating member within the instrument upon penetration into the anatomical cavity can be controlled.

Another object of the present invention is to automatically hold, anchor or stabilize a safety penetrating instrument within an anatomical cavity in response to retraction of a penetrating member to a safe, protected position within the instrument upon penetration into the anatomical cavity with the penetrating member.

It is also an object of the present invention to permit an outer sleeve of a safety penetrating instrument to be automatically or selectively anchored within an anatomical cavity following penetration into the cavity with a penetrating member.

The present invention has an additional object of allowing safe introduction of cannulas, catheters and portal sleeves into body cavities of very small size, such as veins, arteries, spinal, synovial, pleural or pericardial cavities, for example, and for intricate use, such as suprapubic procedures, by automatically retracting a sharp tip of a needle after the cavity is penetrated thereby.

Some of the advantages of the present invention are that small or narrow anatomical cavities can be safely penetrated, an outer sleeve, such as a cannula, catheter or portal sleeve, can safely be introduced into anatomical cavities of very small size for many various procedures in many areas including, for example, cardiac, breast, brain, vascular, chest, genitourinary, suprapubic, neuromuscular, skeletal and spinal fields, safe penetration of cavities can be accomplished with no parts of the safety penetrating instrument other than the outer sleeve protruding into the anatomical cavities upon penetration therein as is particularly desirable where organ structures adhere to cavity walls or the cavities are very small or narrow, the risk of developing a hemaroma when penetrating veins and arteries is reduced, the penetrating member can be gradually advanced within an anatomical cavity following retraction and the distance that the penetrating member protrudes into the cavity can be manually controlled in accordance with procedures to be performed, the automatic retractable safety penetrating instrument can be used in many various ways including, for example, as an infusion or aspiration syringe, an intravenous needle system, an insufflation needle, a catheter system, a biopsy system, an injection or irrigation system, an aspiration or drainage system, catherization for blood, urine, bile, ovarian fluid, spinal fluid, pleural fluid and bowel or peritoneal fluid sampling, with the use of hollow penetrating members, various instruments, such as lasers, can be introduced through the penetrating member, many various surgical procedures can be simplified and enhanced with automatic or selective anchoring or stabilizing of the outer sleeves upon penetration into anatomical cavities, with the outer sleeves stabilized, various medical procedures can be performed through the lumens of the outer sleeves, electric current can be transmitted along a component of the instrument for performing various electrosurgical procedures, including electric coagulation, electric cautery and electric cutting, where safety probes or shields are utilized, the probes or shields can remain extended within anatomical cavities to create, form or maintain a space between walls of the cavities and layers of tissue within the cavities, the automatic retractable safety penetrating instrument encourages the use of a smooth, continuous penetrating motion by the surgeon thereby reducing trauma, tears and irregular surfaces in the tissue of the cavity wall, the automatic retractable safety penetrating instrument can be used to penetrate anatomical cavities of the type containing organ structures that could be injured by contact with even a blunt instrument part such as a safety probe, with use of a safety probe or a safety shield, the sharp tip of the penetrating member can be protected prior to penetration of tissue ensuring safety of medical personnel during use, with the use of a needle having a threaded tip, penetration of the narrowest of anatomical cavities can be achieved in a safe manner in view of the gradual advancement of the needle coupled with immediate, automatic retraction of the needle upon entry of the distal end of the instrument into the cavity, with the use of a curved needle, penetration can be achieved with a spoon-like, scooping or curving motion, the automatic retractable safety penetrating instrument can be provided and stored in a rest state with the sharp distal tip of the penetrating member withdrawn into the outer sleeve and with bias devices in relaxed states, locked and retracted states for the penetrating member can be visually, tactilely and aurally confirmed, fluid flow through the instrument can be visually detected, safe penetration is achieved while permitting injection or evacuation of fluids, trauma and damage to tissue is minimized, tissue jamming and trapping is avoided and automatic safety penetrating instruments according to the present invention can be inexpensively manufactured to be reusable or disposable for universal use.

The present invention is generally characterized in a retractable safety penetrating instrument including a cannula, a penetrating member slidably disposed within the cannula and a hub mounting proximal ends of the penetrating member and cannula. The penetrating member is movable to an operative state with a sharp tip of the penetrating member protruding beyond a distal end of the cannula to penetrate tissue, and is retracted within the cannula upon penetration through the tissue. The penetrating member is selectively movable following retraction to various extended positions with the sharp tip extending beyond the distal end of the cannula to perform various medical procedures with the penetrating member. The cannula can include various expandable, inflatable or shape changing devices for stabilizing the instrument relative to the tissue, and the instrument can be stabilized selectively or automatically in response to retraction of the penetrating member. A safety shield can be slidably disposed between the cannula and the penetrating member or a safety probe can be slidably disposed within the penetrating member with the safety shields and probes biased to extend beyond the distal end of the cannula with the penetrating member in the retracted position. Methods of performing surgical procedures according to the present invention are characterized in the steps of automatically retracting a sharp tip of a penetrating member within a cannula in response to positioning of the cannula in tissue, moving the penetrating member distally to cause the sharp tip to protrude beyond a distal end of the cannula and performing a procedural step with the penetrating member.

These and other objects and advantages of the present invention will become apparent from the following description of the preferred embodiments taken in conjunction with the accompanying drawings wherein identical reference numbers indicate identical parts or parts providing identical functions.

BRIEF DESCRIPTION OF THE DRAWINGS

FIG. 1 is a top plan view of an automatic retractable safety penetrating instrument according to the present invention.

FIG. 2 is a section taken along line 2—2 of FIG. 1.

FIG. 3 is a section taken along line 3—3 of FIG. 2.

FIG. 4 is a broken, top sectional view of the automatic retractable safety penetrating instrument of FIG. 1 with the penetrating member in an operative position prior to penetrating tissue of an anatomical cavity wall.

FIG. 5 is a broken, top sectional view of the automatic retractable safety penetrating instrument of FIG.

1 during triggering of the retraction mechanism following penetration into the anatomical cavity.

FIG. 6 is a broken, top sectional view of the automatic retractable safety penetrating instrument of FIG. 1 with the penetrating member in a retracted position.

FIG. 7 is a broken side view, partly in section, of a modification of an automatic retractable safety penetrating instrument according to the present invention prior to penetrating tissue of an anatomical cavity wall.

FIG. 8 is a broken side view of a distal end of the automatic retractable safety penetrating instrument of FIG. 7.

FIG. 9 is a broken side view, partly in section, of the automatic retractable safety penetrating instrument of FIG. 7 in an operative state during penetration of the cavity wall.

FIG. 10 is a broken side view, partly in section, of the automatic retractable safety penetrating instrument of FIG. 7 during triggering of the retraction mechanism following penetration into the anatomical cavity.

FIG. 11 is a broken side view, partly in section, of the automatic retractable safety penetrating instrument of FIG. 7 with the penetrating member in a retracted position.

FIG. 12 is a broken side view, partly in section, of another modification of an automatic retractable safety penetrating instrument according to the present invention.

FIG. 13 is a broken side view of a distal end of the automatic retractable safety penetrating instrument of FIG. 12.

FIG. 14 is a broken side view, partly in section, of the automatic retractable safety penetrating instrument of FIG. 12 with the penetrating member in a retracted position following penetration into an anatomical cavity.

FIG. 15 is a broken sectional view of a modification of a hub arrangement for the automatic retractable safety penetrating instruments of the present invention.

FIG. 16 is a broken perspective view of another modification of a hub arrangement for the automatic retractable safety penetrating instruments according to the present invention.

FIG. 17 is a broken side view, partly in section, of an additional modification of an automatic retractable safety penetrating instrument according to the present invention.

FIG. 18 is a side view of a further modification of an automatic retractable safety penetrating instrument according to the present invention.

FIG. 19 is a broken side view, partly in section, of an additional modification of an automatic retractable safety penetrating instrument according to the present invention.

FIG. 20 is a broken side view, partly in section, of the automatic retractable safety penetrating instrument of FIG. 19 with the penetrating member in a retracted position.

FIG. 21 is a broken side view, partly in section, of a further modification of an automatic retractable safety penetrating instrument according to the present invention.

FIGS. 22, 23 and 24 are broken side views, partly in section, of modifications of the distal ends of the penetrating members for the automatic retractable safety penetrating instruments of the present invention.

DESCRIPTION OF THE PREFERRED EMBODIMENTS

An automatic retractable safety penetrating instrument 30 according to the present invention is illustrated in FIG. 1 and includes an elongate penetrating member or needle 32, an outer sleeve or cannula 34 concentrically disposed around the needle and a hub 36 mounting the needle 32 and the cannula 34. Needle 32 is preferably made of a medical grade material, such as stainless steel, and has an outer diameter or size dependent upon the surgical procedure to be performed and the anatomical cavity to be penetrated. The needle 32 has a distal end 38 terminating at a sharp tip 40 for penetrating anatomical tissue. The needle 32 can be solid or cannulated, and the distal end 38 can have various hollow or solid geometrical configurations. As shown in FIG. 1, the needle 32 is hollow or cannulated with an open distal end having an angled distal end surface 42 disposed at an angle with a longitudinal axis of the needle and terminating distally at sharp tip 40 and proximally at a trailing edge 44 joined to an elongated body 46 which can be cylindrical or have any desirable configuration in cross-section. Body 46 extends proximally from the trailing edge 44 to terminate at an operating member or flange 48 at a proximal end of the needle, the proximal end being disposed in hub 36 with body 46 passing through an aperture in a front wall of the hub. The body can be hollow or tubular along the length of the needle, or the body can be partly hollow or tubular to receive a tube 50 extending distally through an aperture in a rear wall of the hub and into the hollow proximal end of the needle with the tube 50 being coupled with a valve housing 52 disposed externally of the hub 36. An operating bias device or spring 54 is connected between operating flange 48 and a retraction plate 56, the plate having an aperture therethrough receiving the proximal end of the needle. A retracting bias device or spring 60 is connected between the rear wall of hub 36 and retraction plate 56. The operating bias device or spring 54 is formed as a resilient, tubular sleeve from material, such as rubber, elastic or sponge, and is in a contracted, relaxed or unloaded state, as shown in FIG. 3, biasing the needle distally to an extended position, as shown in FIG. 1, wherein the sharp tip 40 protrudes beyond a distal end of the cannula 34. The retracting bias device or spring 60 is formed by an elastic, solid rubber or sponge member secured to the rear wall of hub 36 and to retraction plate 56 so as to be in tension or stretched when in the position shown in FIG. 3 to bias the retraction member 58 proximally.

Hub 36 can be made of any suitable material to be disposable or reusable and has an external configuration to be easily grasped with one hand for use in penetrating tissue. Hub 36 can have any desired configuration in cross-section and is shown in FIG. 2 as being substantially rectangular while having a flared profile adjacent the front wall thereof to facilitate grasping during use. The rear wall of the hub can be removable allowing the needle to be removed from the cannula with removal of the needle and replacement of the rear wall on the hub being facilitated by use of a module for the retracting mechanism and the locking and releasing mechanism as explained further below. A top wall 62 of the hub has a central recessed channel 64 aligned with a longitudinal axis of the automatic retractable safety penetrating instrument, and a slot 66 is disposed in the channel 64 and is formed of a longitudinal slot portion 68 aligned with the longitudinal axis of the instrument 30, a distal transverse slot portion 70, an intermediate transverse slot portion 72 and a proximal transverse slot portion 74, as best shown in FIG. 1. A pin 76 is threadedly secured in the periphery of operating flange 48 and extends through slot 66, as best shown in FIG. 2, the pin having a "T" configuration to terminate at an external knob 78. The pin can be mounted on the penetrating member at any suitable location, and the slot can be mounted at any suitable location along the hub depending upon the retracting mechanism and locking and releasing mechanism utilized in the automatic retractable safety penetrating instrument.

A retracting mechanism engages the proximal end of the needle 32 and includes the retracting plate 56 and the retracting spring 60, and the retracting mechanism is actuated by a locking and releasing or trigger mechanism 80 formed of a latch or locking spring having a substantially flat base 82 secured to a wall of hub 36 with an arm 84 bent inwardly therefrom and extending angularly distally in the direction of the longitudinal axis. A bent locking finger or member 86 is carried on a distal end of arm 84 to engage retraction plate 56 and hold the plate against the front wall of the hub to prevent movement thereof when the locking spring is in its normal position as illustrated in FIG. 3. The trigger mechanism 80 has a releasing or trigger member 88 extending rearwardly or proximally from arm 84 at an angle to allow movement of operating flange 48 thereby in a proximal direction without causing bending of arm 84. The retracting spring or bias device 60 defines a shoulder 90 acting as a positive stop or abutment member to limit proximal movement of the needle by abutment with operating flange 48, and trigger 88 is positioned distally of shoulder 90 by a distance corresponding to the distal movement desired of the operating member or flange prior to automatic retraction, as will be explained in more detail hereinafter. The locking and releasing or trigger mechanism can be mounted at any suitable location on the hub and provided with any required configuration to act as a stop or abutment to prevent proximal movement of the retracting plate and to be actuated or released by the distally moving operating member. The locking and releasing mechanism can be made as one piece or multiple pieces dependent upon the hub construction and the operating member utilized to actuate the trigger, flange 48 in the embodiment of FIG. 1. As shown, locking member 86 and trigger 88 are unitarily, integrally formed of a single strip of resilient, spring material such as metal or plastic. The locking and releasing mechanism as well as the retraction mechanism can be formed as a module to simplify assembly in the hub as explained in applicant's co-pending patent application Ser. No. 07/848,838, filed Mar. 10, 1992, the specification of which is incorporated herein by reference.

Outer sleeve 34 is preferably made of a substantially cylindrical length of rigid or flexible material, such as stainless steel or other suitable, medical acceptable, plastic or metal material, and can be transparent or opaque. The outer sleeve can be a cannula, catheter or portal sleeve and, as shown in FIG. 1, the outer sleeve is a cannula having a distal end 92 with a configuration to produce a smooth profile with the angled end surface of the needle when the instrument is in an operative state to penetrate tissue, and the cannula has a proximal end mounted in or formed with a front wall of the hub 36 with a lumen extending between the distal and proximal ends. A distal portion of the cannula is made of a shape memory material, such as a resilient plastic or spring metal, and has a normal, predetermined, nonlinear configuration, including curved, bending or convoluted configurations, such as the hook or "J" shaped configuration shown in FIG. 6, while being substantially linear when the needle is disposed in the lumen thereof in the operative position as will be explained further below.

Housing 52 can be made of any suitable material to be disposable or reusable and has a configuration in cross-section cooperating with the cross-sectional configuration of the hub to facilitate grasping during use. The housing can be formed integrally, unitarily with or separately from the rear wall of the hub and includes a body defining a chamber 94 communicating with the lumen of the tube 50 and a branch connector 96 having a passage communicating with the chamber and axially aligned with the lumen of the tube extending outwardly from the housing body. A valve assembly 98 is provided in the passage of the branch connector to control flow of fluid through the housing. The valve assembly can have various configurations and arrangements and, is shown in FIG. 1 as a stop cock; however, various other valve assemblies can be provided on or in the housing to control fluid flow as well as to allow surgical instruments to be inserted through the needle while creating a seal with the instruments. One or more branch connectors can be provided for various uses, such as infusion ports, aspiration ports, simultaneous infusion of different fluids, instrument passages, and a valve assembly can be provided for each branch connector. The housing body is made of a transparent material, and a floating ball 100 is disposed in the chamber 94 to be visible through the housing body to serve as an indicator for fluid flow through the housing.

In use, the automatic retractable safety penetrating instrument 30 is normally provided in a rest state wherein the distal end of the needle 32 is retracted within the cannula 34 to be in a safe protected condition, the rest state coinciding with the retracted position for the needle, shown in FIG. 6. In the rest state, the retracting spring 60 is in a relaxed, unbiased or unloaded state, and the retraction plate 56 is moved proximally carrying with it the needle 32 such that the sharp tip 40 of the needle is disposed within the cannula, it being noted that the operating spring 54 is similarly in an unbiased state in the rest position. Accordingly, with the automatic retractable safety penetrating instrument initially provided in a rest state, no loading of the springs exists such that the strength of the springs is not weakened and shelf life is increased. With the automatic retractable safety penetrating instrument in the rest state, the pin 76 will be disposed at a proximal end of the longitudinal slot portion 68 and can be moved via knob 78 to be received in the proximal transverse slot portion 74 to be locked in that position to assure that the sharp distal end of the needle remains in a protected position. By forming operating flange 48 separate from the needle and rotatably mounting the flange on the proximal end of the needle, the pin can be rotated into the proximal transverse slot portion without rotation of the needle. When it is desired to utilize the instrument 30 to penetrate tissue to introduce the cannula into an anatomical cavity, the knob 78 is grasped and moved distally along the longitudinal slot portion 68 to the distal end thereof causing the retraction plate 56 to move over arm 84 and finger 86 to be locked in place adjacent the front wall of the hub, as shown in FIG. 3, with the locked state corresponding to the extended condition shown in FIG. 1. Locking of the retraction plate can be confirmed by feel and sound as the locking member snaps into place and also visually by viewing the position of the knob 78 relative to the slot 66. Additionally, the proximal end of the needle can be made a first, predetermined color and the tube 50 can be made a second, different, predetermined color with the hub being made transparent along the recessed channel or at any suitable location to view the tube. Accordingly, the color of the needle proximal end will be visible through the hub when the needle is in the retracted position and the color of the tube will be visible through the hub when the needle is in the extended position and; therefore, locking of the retraction plate can be confirmed visually by observance of a color change through the hub. With the instrument in the extended condition, the trailing edge 44 of the needle will be spaced from the distal end 92 of the cannula by a distance that is the same as the spacing between flange 48 and stop or abutment member 90.

The instrument 30 can now be utilized to penetrate tissue and enter an anatomical cavity in three manners. In a first manner, the pin 76 is moved into the distal transverse slot portion 70 which allows the instrument to be used as a standard penetrating instrument since the needle is prevented from retracting. In a second manner, the hub is grasped by the surgeon and the instrument is forced against tissue T, such as a wall of an anatomical cavity, as shown in FIG. 4, causing the needle 32 to move proximally against the bias of operating spring 54 until flange 48 abuts stop member 90 at which time the needle will be in the operative position with the trailing edge 44 aligned with the distal end 92 of the cannula, as shown in FIG. 4. When the flange or operating member 48 moves proximally, the operating member causes trigger member 88 to deflect proximally such that the flange 48 moves proximally past the trigger member, as shown in FIG. 4. While the trigger member 88 is shown in FIG. 4 as being closely adjacent or abutting flange 48, trigger member 88 can be positioned at varying distances from flange 44 to control the amount of distal movement of the operating member required before the needle is retracted. In a third manner of operation, the needle is manually moved to the operative position by grasping knob 78, moving the pin 76 proximally in the longitudinal slot portion 68 and then positioning the pin in the intermediate transverse slot portion 72 to maintain the needle in the operative position with the trailing edge 44 in alignment with the cannula distal end 92. In either of the second or third manners, after the needle is moved to the operative position, the instrument is forced through the tissue T to enter the anatomical cavity with the sharp distal tip 40 of the needle extending beyond the distal end 92 of the cannula with the distal end of the instrument having a configuration of a standard penetrating instrument; and, once the distal end of the instrument has passed through the tissue T, operating spring 54 will move needle 32 distally causing distal movement of operating member 48 to engage trigger member 88 and flex arm 84 downwardly looking at FIG. 5 such that locking member 86 is moved out of abutment with retraction plate 56. Accordingly, retracting spring 60 will automatically move the retraction plate and the needle to the retracted position shown in FIG. 6 with the sharp distal tip 40 of the needle within the cannula in a safe protected position.

When the third manner of operation is utilized, the surgeon can merely utilize his finger to move the pin 76 out of the intermediate transverse slot portion 72 once tissue penetration has begun thereby allowing retraction upon entry into the anatomical cavity while in the second manner of operation, the knob will continuously remain in the longitudinal slot portion 68 to produce automatic retraction. If desired, the pin can remain in the intermediate transverse slot portion 72 preventing automatic retraction similar to the first manner of operation described above. Retraction of the needle and, therefore, penetration of the cannula into the anatomical cavity, can be confirmed by sound and feel and visually by movement of the pin 76 along the slot 66. Additional visual confirmation can be obtained by observing a color change through the hub as the color of the needle proximal end becomes visible over the tube.

Once the distal end of the instrument has entered into the anatomical cavity and the needle has moved to the retracted position, the pin 76 may be moved into the proximal transverse slot portion 74 to lock the needle in the retracted position or the needle can remain in the retracted position from force of the retracting spring 60. The knob 78 may be grasped to move the pin 76 distally along the longitudinal slot portion 68 to position the needle in an extended position with the sharp tip disposed in the anatomical cavity beyond the distal end of the cannula to perform various medical procedures within the cavity. The needle can be maintained in an extended position with pressure on knob 78 as well as by moving the pin into the distal or intermediate transverse slot portions. Additional intermediate transverse slot portions can be provided along slot 66 to define various, incremental extended positions for the needle at which positions the needle can be locked in place. A source of fluid or vacuum can be coupled with the branch connector 96 and, via opening of the valve assembly 98, fluid can be supplied to or aspirated from the anatomical cavity through the lumen of the needle. Fluid flow through the instrument can be visually detected or confirmed by viewing movement of the ball 100 within the chamber 94 through the body of the housing 52. With the needle in the retracted position, the distal portion of the cannula will automatically change shape, returning to the predetermined non-linear configuration with the hook or "J" shaped configuration of the distal end portion holding, anchoring or stabilizing the instrument within the cavity. The needle can be withdrawn from the cannula allowing the cannula to remain in place within the body cavity for conducting various procedures through the cannula. One or more apertures can be provided in the distal end of the portal sleeve establishing fluid communication with the anatomical cavity. The instrument 30 is particularly advantageous for use in lumpectomy procedures in that the cannula can be left in place and stabilized at the site of a lump and, thereafter, an instrument for performing a lumpectomy can be inserted through the instrument. The non-linear, J-shape configuration of the distal portion of the cannula is particularly suitable for use in tissue, such as breast tissue, that is friable. The predetermined non-linear configuration can have various shapes and can extend in various directions in accordance with the anatomical structure of the cavity and the procedure to be performed. Where the instrument is used as a standard penetrating instrument without retraction, the pin 76 can be moved to the proximal transverse slot portion 74 upon penetration of the cannula distal end portion into the cavity to selectively anchor or stabilize the instrument within the cavity.

A connection or attachment 104 for transmitting electrical current can be provided on knob 78 and the needle 32 along with the flange 48, pin 76 and knob 78 can be made of an electrically conductive material while the rest of the instrument is made from insulative or non-conductive materials. In this manner, electric current can be transmitted along the needle for performing various electrosurgical procedures, such as electric cautery, electric coagulation and electric cutting, with the needle. By forming the cannula of insulative material, electrosurgical procedures can be conducted in anatomical cavities with greater precision and control due to the gradual advancement of the needle and with increased safety due to the protection afforded by the cannula to tissue and structure within the cavity.

While resilient, elastic bias devices are shown in the instrument 30 with the retracting spring axially offset from the longitudinal axis of the instrument and the operating spring concentric therewith and surrounding the needle, many different arrangements and types of springs or bias devices can be utilized with the present invention with the bias devices having loaded or biased states in either compression or tension, and the various bias devices and springs disclosed in applicant's co-pending patent applications referenced hereinabove and incorporated herein by reference can be used with the present invention.

A modification of an automatic retractable safety penetrating instrument according to the present invention is illustrated in FIG. 7 at 130. The automatic retractable safety penetrating instrument 130 includes a cannulated penetrating member or needle 132 having an open distal end 138 with an angled distal end surface 142 terminating distally at a sharp distal tip 140 and proximally at a trailing edge 144 joining the distal end to a body 146. The body 146 terminates proximally at an operating member or flange 148 at a proximal end of the needle, the proximal end being disposed in hub 136 with body 146 passing through an aperture in a front wall of the hub. A tube 150 extends distally through a removable rear wall of the hub and into the proximal end of the needle to guide proximal movement of the needle therealong. A coiled helical operating spring 154 is concentrically disposed around the body 146 and connected between the operating flange 148 and a retraction plate 156 of a retracting member 158, the plate having an aperture therethrough receiving the proximal end of the needle and joining a rail arrangement 159 forming a recess for receiving a coiled, helical retracting spring 160 connected between the rear wall of the hub and retraction plate 156. If required, a guide rod 161 can extend from the rear wall of the hub to the front wall of the hub passing through retraction plate 156 to provide a guide to maintain the retracting spring 160 in axial alignment. Tube 150 terminates externally of the hub 136 to define a passage communicating with and axially aligned with the lumen of the needle. A valve assembly 198 is mounted along the tube 150 externally of the hub to control fluid flow or the insertion of instruments, such as a laser, through the instrument 130. A pin (not shown) can be provided in the periphery of the operating flange 148 to be received in a slot (not shown) formed in the hub 136 and having a longitudinal slot portion, a distal transverse slot portion, a proximal transverse slot portion and one or more intermediate transverse slot portions with one of the intermediate transverse slot portions corresponding to the operative position for the instrument 130.

A retracting mechanism engages the proximal end of the needle and includes retraction plate 156, retracting member 158 and retracting spring 160, and the retracting mechanism is actuated by a locking and releasing or trigger mechanism 180 similar to the locking and releasing or trigger mechanism 80. The guide rail 159 terminates proximally at a stop or abutment member 190 acting as a positive stop or abutment to limit proximal movement of the needle by abutment with operating flange 148, and trigger 188 is positioned distally of stop member 190 by a distance corresponding to the distal movement desired of the flange or operating member 148 prior to automatic retraction. The retraction plate 156 is joined to an elongate middle member 133 disposed between the needle and the cannula. The cannula 134 has a proximal end mounted in or formed with a front wall of the hub and a distal end 192 with a configuration to produce a smooth profile with the angled distal end of the needle when the needle is in the operative position. The cannula is formed of a distal portion 135 and a body 137 joined or connected with the distal portion by a plurality of resilient strips 139 disposed substantially parallel with a longitudinal axis of the instrument 130 and substantially aligned with the circumference or periphery of the cannula in a non-expanded, contracted or collapsed state, as shown in FIGS. 7 and 8. If desired, a flexible, elastic or resilient membrane of minimal thickness can be provided on the cannula to cover the strips and prevent tissue from being caught therebetween. The strips 139 are biased in a direction outwardly from the longitudinal axis of the automatic retractable safety penetrating instrument 130 to be normally disposed outwardly of the circumference of the cannula in an expanded state with the strips bent along hinges 141 radially aligned with the longitudinal axis, as shown in FIG. 11. An internal shoulder or abutment wall 143 is formed along an inner surface of the cannula at a proximal end of the distal portion 135, and the portion is urged toward the body 137 due to the bias of strips 139. The strips 139 are maintained in the non-expanded or collapsed state by abutment of the middle member 133 with the abutment wall 143 such that the cannula is substantially linear when the middle member is in the position shown in FIG. 7. The middle member 133 can be tubular or can have any other desired configuration in cross-section, and the length of the middle member is selected to maintain the strips in the collapsed state via abutment of wall 143 with a distal end of the middle member when the retraction plate 156 is held against the front wall of the hub, the middle member preventing movement of the distal portion 135 toward the body 137.

In use, the automatic retractable safety penetrating instrument 130 is normally provided in a rest state coinciding with the retracted position for the needle shown in FIG. 11. In the rest state, retracting spring 160 is in a relaxed, unbiased or unloaded state and the retraction member 158 is moved proximally until stop member 190 abuts the rear wall of the hub 136 carrying with it the needle 132, it being noted that operating spring 154 is similarly in an unbiased state in a rest position and the pin is disposed at a proximal end of the longitudinal slot portion. With the automatic retractable safety penetrating instrument 130 in the rest state, the pin can be rotated in the proximal transverse slot portion to be locked in that position to assure that the sharp distal end 140 of the needle 132 remains in a protected position. When it is desired to utilize the instrument 130 to penetrate tissue to introduce the cannula 134 into an anatomical cavity, the pin is moved, via the knob, distally within the longitudinal slot portion to the distal end thereof causing the retraction plate 156 to move over arm 184 and finger 186 of locking and releasing mechanism 180 to be locked in place adjacent the front wall of the hub with the needle in the extended condition, as shown in FIG. 7. Locking of the retraction plate 156 can be confirmed by feel and sound as the locking member 186 snaps into place and also visually by viewing the position of the knob relative to the slot as well as collapse or straightening of the cannula 134 as the distal end of the middle member 133 engages the abutment wall 143 and moves the distal portion 135 further from the body 137. Where the proximal end of the needle 132 and the tube 150 are of different colors and a portion of the hub 136 overlying the tube is transparent, locking can be confirmed visually by observing a color change through the hub. With the instrument 130 in the extended condition shown in FIG. 7, the trailing edge 144 of the needle will be spaced from the distal end 192 of the cannula by a distance that is the same as the spacing between the operating flange 148 and the stop or abutment member 190.

Operation of instrument 130 is similar to that described for instrument 30. In a first manner of operation, the pin is rotated into the distal transverse slot portion which allows the instrument 130 to be used as a standard penetrating instrument since the needle is prevented from retracting. In a second manner of operation, the hub 136 is grasped by the surgeon and the instrument 130 is forced against tissue T, such as a wall of an anatomical cavity, as shown in FIG. 9, causing needle 132 to move proximally against the bias of operating spring 154 until flange 148 abuts stop member 190 at which time the needle will be in the operative position with the trailing edge 144 of the needle aligned with the distal end 192 of the cannula 134, as shown in FIG. 9. When the flange or operating member 148 moves proximally, the operating member causes trigger member 188 to deflect proximally such that the flange moves proximally past the trigger member, as shown in FIG. 9. In a third manner of operation, the needle is manually moved to the operative position by grasping the knob, moving the pin proximally in the longitudinal slot portion and then positioning the pin in the intermediate transverse slot portion to maintain the needle in the operative position with the trailing edge 144 in alignment with the portal sleeve distal end 192. In either of the second or third manners, after the needle is moved to the operative position the instrument is forced through the tissue T to enter the anatomical cavity with the sharp distal tip 140 of the needle extending beyond the distal end of the cannula; and, once the distal end of the instrument has passed through the tissue T, operating spring 154 will move the needle distally causing distal movement of operating member 148 to engage trigger member 188 and flex arm 184 downwardly looking at FIG. 10 such that locking member 186 is moved out of abutment with retraction plate 156. Accordingly, retracting spring 160 will automatically move the retracting member 158 and, therefore, the middle member 133 and the needle 132 to the retracted position shown in FIG. 11 with the sharp distal tip 140 of them within the cannula 134 in a safe, protected position. When the third manner of operation is utilized, the surgeon can merely utilize his finger to move the pin out of the intermediate transverse slot portion once tissue penetration has begun thereby allowing retraction upon entry into the anatomical cavity while in the second manner of operation, the knob will continuously remain in the longitudinal slot portion to produce automatic retraction. If desired, the pin can remain in the intermediate transverse slot portion preventing automatic retraction similar to the first manner of operation described above. Once the distal end of the instrument 130 has entered into the anatomical cavity and the needle 132 and the middle member 133 have moved to the retracted position, the distal end of the middle member will have moved proximally of the abutment wall 143 such that the strips 139 are automatically disposed in the expanded state with the strips bent along hinges 141 and disposed outwardly from the circumference of the cannula body to anchor, hold or stabilize the instrument within the anatomical cavity. Thereafter, the pin can be moved distally along the longitudinal slot portion allowing the tip 140 of the needle 132 to be extended beyond the distal end 192 of the cannula 134 to perform various procedures with or through the needle while the cannula remains stabilized. Various intermediate transverse slot portions can be provided in the hub 136 allowing the needle to be locked in various intermediate extended positions with the sharp tip protruding beyond the distal end of the cannula into the anatomical cavity, and the distance that the sharp tip of the needle protrudes beyond the distal end 192 of the cannula 134 in the intermediate extended positions can be less than the distance that the sharp tip protrudes beyond the portal sleeve in the operative condition such that the cannula remains stabilized within the anatomical cavity. Where the instrument 130 is utilized as a standard penetrating instrument without retraction of the needle, the pin can be moved to a proximal end of the longitudinal slot portion upon penetration into the anatomical cavity to allow the strips to move to the expanded position thusly providing selective anchoring or stabilization.

Another modification of an automatic retractable safety penetrating instrument according to the present invention is illustrated at 230 in FIG. 12. The retracting member 258 and the locking and releasing mechanism 280 for the instrument 230 are similar to that shown in FIG. 7 except that the trigger member 288 is formed of a cam having opposing legs 289 and 291, the trigger member being rotatable or pivotably mounted on a pin 293 extending between side walls of the hub 236 or of a case as disclosed in applicant's co-pending patent application Ser. No. 07/848,838 filed Mar. 10, 1992, the specification of which is incorporated herein by reference. The cannula 234 has a distal end 292 configured to form a smooth profile with the needle 232 in the operative state and a proximal end mounted in or formed with a front wall of the hub 236. The distal portion 235 of the cannula 234 is joined to the cannula body 237 by an axial length of a circumferentially or peripherally continuous flexible balloon, membrane or tube 239. The balloon 239 is normally disposed in a contracted, non-inflated or non-expanded state substantially continuous with the circumference of the distal portion 235 and body 237 as shown in FIGS. 12 and 13. A passage 241 is formed in the wall of the cannula body 237 to extend longitudinally, axially from the balloon 239 to the hub 236, the passage 241 opening into the interior of the hub through the front wall thereof. A valve or seal 243 is mounted on a forward face of the retraction plate 256 to close off and seal the passage from the interior of the hub when the retraction plate is held against the front wall via the locking and releasing mechanism 280, as shown in FIG. 12. A valve 297 is provided in a wall of the hub 236 to control flow of fluid and, therefore, pressurization, in the interior of the hub.

The automatic retractable safety penetrating instrument 230 can be used to penetrate tissue of an anatomical cavity wall in manners similar to those described above for instrument 130 in that retraction member 258 is locked against proximal movement by engagement of locking member 286 with retraction plate 256 while needle 232 can move proximally against the bias of operating spring 254. Once the operating flange 248 has moved to a position in abutment with the stop member 290, the trailing edge 244 of the needle 232 will be aligned with the distal end 292 of the cannula 234 such that the needle is in the operative state. Valve 297 is opened to supply fluid, such as air, to the interior of the hub thusly pressurizing the hub while the passage 241 remains sealed from the hub interior by valve 243. Upon penetration into an anatomical cavity, distal movement of the needle from the bias of operating spring 254 will cause the operating flange 248 to engage leg 289 of trigger cam member 288 pivoting the cam and causing the leg 291 to engage and flex arm 284 to move locking member 286 out of abutment with retraction plate 256 thereby allowing retracting spring 260 to move the retraction member 258 and the needle 232 to the retracted position with the sharp distal tip 240 of the needle within the cannula. Proximal movement of the retraction plate 256 results in valve 243 being unseated from passage 241 such that fluid under pressure in hub 236 automatically flows through the passage to inflate or expand the balloon 239, the balloon being shown in the expanded state in FIG. 14. Where the automatic retractable safety penetrating instrument 230 is utilized as a standard penetrating instrument, selective anchoring can be obtained upon penetration by moving the retraction plate 256 away from the front wall of the hub to open the passage 241. In the expanded state, the balloon anchors or stabilizes the instrument 230 within the anatomical cavity and also creates a seal with the wall of the cavity allowing various procedures to be conducted through the lumen of the needle or the lumen of the cannula where the needle is withdrawn. The automatic retractable safety penetrating instrument 230 is particularly useful in creating a seal within anatomical cavities, and is particularly advantageous in procedures for draining the gall bladder common duct wherein the balloon creates a seal with the cavity wall while fluid is drained via aspiration through the instrument 230. The passage 241 can have any suitable configuration and can be annular, concentric with the wall of the cannula and the valve 243 can have any configuration to cooperate with the configuration of the passage to close off and seal the passage when retraction plate 256 is held against the front wall of the hub.

A modification of a hub arrangement 336 for use with the automatic retractable safety penetrating instruments of the present invention is illustrated in FIG. 15 wherein, for simplification, the locking and releasing mechanism is not shown. The operating flange 348, operating spring 354, retracting mechanism 358 and retracting spring 360 are similar to those shown in FIG. 14. A thread 359 is disposed along an inner surface of the hollow proximal end of the needle 332, and an end of the tube 350 disposed in the proximal end of the needle has a complementary thread 361 formed thereon for matingly engaging the thread 359 on the needle.

Operation of the modification of FIG. 15 is similar to that described above for instrument 230 in that, upon penetration into an anatomical cavity, the retracting mechanism 358 carries with it the needle 332 to the retracted position wherein the sharp tip of the needle is disposed within the cannula. Thereafter, the tube 350 can be grasped, from externally of the hub 336, and the thread 361 on the tube 350 engaged with the thread 359 on the needle 332 to couple the tube with the needle. The tube 350 can then be gradually moved distally and proximally to position the needle 332 in various extended positions with the distal end of the needle protruding from the distal end of the cannula and into an anatomical cavity, and the amount and speed of advancement of the needle beyond the distal end of the cannula can be controlled via manual movement of the tube. In FIG. 15, the electric connector 304 is shown as being mounted on the tube 350 externally of the hub 336; and, by forming the tube 350 and the needle 332 of electric conductive material, electric current can be transmitted along the needle via the connector 304 for performing electrosurgical procedures. By forming the cannula, as well as other components of the instrument, of insulative material, electrosurgery can be performed with greater safety, precision and control.

Another modification of a hub arrangement for use with the automatic retractable safety penetrating instruments of the present invention is illustrated at 436 in FIG. 16 wherein only the rear wall of hub 436, the proximal end of the needle 432 and a portion of the tube 450 are shown. The end of the tube 450 disposed in the hollow proximal end of the needle 432 carries a first pair of lugs 451 at a distalmost end of the tube and a second pair of lugs 453 proximally spaced from the first pair of lugs 451. The lugs 451 are positioned at 180° spaced locations on the tube, and the lugs 453 are positioned at 180° spaced locations on the tube offset from the lugs 451 by 90°. Slots 455 are formed in the operating flange 448 around tube 450 at 180° spaced locations with the tube being rotatable within the needle 432. Accordingly, the tube can be rotated to align the lugs 453 with the slots 455 allowing the lugs 453 to be withdrawn from the needle and, by rotating the lugs 453 out of alignment with the slots 455, the lugs can be positioned against a rearward facing surface of the flange 448. Thereafter, the tube 450 can be moved distally to push the needle in a distal direction to position the needle at various extended positions relative to the cannula. When it is desired to move the needle proximally from the extended positions, the tube is rotated and moved proximally to engage a forward facing surface of the flange 448 with the lugs 451 allowing the needle to be moved proximally. Various indicia can be provided on the instrument to indicate the position of the lugs relative to the slots.

Another modification of an automatic retractable safety penetrating instrument according to the present invention is shown at 530 in FIG. 17 and includes cannula 534 mounted in or formed as part of the front wall of the hub 536, needle 532 disposed within the cannula and a safety probe 565 slidably disposed within the lumen of the needle. The needle 532 terminates proximally at a flange 556 operating as a retraction plate and joining a rail guide 559 having an L-shape in cross-section with a proximal flange or stop member 590, the retraction plate being locked in place against a front wall of the hub by the locking finger 586 of a locking and releasing mechanism 580. Retraction member 558 formed by plate 556 and rail guide 559 can be formed as one piece with needle 532 or can be a separate member fastened thereto in any suitable manner. With the retraction plate 556 locked against the front wall of the hub 536, the needle 532 is in an operative state with the trailing edge 544 aligned with the distal end 592 of the cannula 534. The safety probe 565 has a blunt distal end 567 extending beyond the sharp distal tip 540 of the needle 532 in the operative state and can have an aperture 569 therein to allow communication entirely through the instrument 530 where the probe 565 is hollow. The probe 565 has a hollow proximal end 548 with a flange-like configuration to form an operating member for actuating retraction, and the probe is biased distally by an operating spring 554 disposed concentrically around the safety probe and connected between the retraction plate 556 and the operating flange 548. The tube 550 extends distally through a rear wall of the hub 536 and into the hollow proximal end of the safety probe, the tube passing through an aperture in the stop member 590. The retracting spring 560 is disposed concentrically around the tube 550 and connected between the stop member 590 and the rear wall of the hub 536 such that the needle 532 is biased proximally by the spring 560 to a retracted position. The arrangement of the operating spring and the retracting spring in longitudinal coaxial alignment in the hub permits the hub to have minimal width. The locking and releasing mechanism 580 is similar to the locking and releasing mechanism 280 shown in FIG. 12 and has a locking arm 584 carrying a locking member 586 and configured to engage the retraction plate 556 and a trigger cam 588 having legs 589 and 591 for camming the locking arm out of engagement with the retraction plate in response to distal movement of the operating member 548.

The operation of the modification of FIG. 17 is similar to that described above in that retraction member 558 is locked against proximal movement by engagement of locking member 586 with the retraction plate 556 while the safety probe 565 can move proximally against the bias of the operating spring 554. With the retraction member 558 locked by locking member 586, the needle 532 is in the operative state shown in FIG. 17 wherein the trailing edge 544 of the needle is aligned with the distal end 592 of the cannula and the distal end 567 of the safety probe will be disposed beyond the sharp tip 540 of the needle. During penetration of tissue, the safety probe 565 will be moved proximally against the bias of the operating spring 554 until the operating flange 548 is in abutment with the stop member 590 exposing the sharp tip 540 of the needle. Upon penetration into an anatomical cavity, the safety probe 565 will be moved distally from the bias of the operating spring 554 causing the operating member 548 to engage leg 589 of trigger cam 588 pivoting the cam and causing the leg 591 to engage and flex arm 584 to move locking finger 586 out of abutment with the retraction plate 556 thereby allowing retracting spring 560 to move the retraction member 558 and the needle, which carries with it the safety shield, to a retracted position with the sharp distal end of the needle and the distal end of the safety probe disposed within the cannula. The automatic retractable safety penetrating instrument 530 is particularly advantageous in minimizing extension of the instrument into an anatomical cavity upon penetration therein as is particularly useful in penetrating very small or narrow cavities or cavities containing delicate tissue or organ structure that could be damaged by even a blunt instrument.

FIG. 18 illustrates another modification of an automatic retractable safety penetrating instrument 630 according to the present invention. In the modification of FIG. 18, the hub 636 is formed as or coupled with a syringe body 639 for use as an infusion or aspiration syringe to supply fluid to or aspirate fluid from an anatomical cavity via the lumen of the needle 632. The hub 636 can be connected to various other devices, such as bags, bottles and the like, in addition to the syringe body 639, suitable to supply or withdraw fluid through the instrument 630 in irrigation and aspiration procedures. The knob 678 and slot 666 allows the needle 632 to be extended from the cannula 634 following retraction.

Another embodiment of an automatic retractable safety penetrating instrument is illustrated in FIG. 19 at 730 and includes a cannula 734 formed with or connected to a front wall of the hub 736, a needle 732 disposed within the cannula and a safety probe 765 disposed within the lumen of the needle. The safety probe 765 terminates proximally at an end flange 773, with the tube 750 extending distally through a rear wall of the hub 736 and through an opening in the end flange 773 into the hollow proximal end of the safety probe. An annular rim 779 is disposed on an end of the tube 750 within the proximal end of the safety probe, and a helical coil spring 777 is connected between the rim 779 and the end flange 775 to bias the safety probe distally to an extended position with the blunt distal end 767 of the safety probe protruding beyond and protecting the sharp tip 740 of the needle. The needle terminates proximally at an operating member or flange 748 disposed within the hub, with the needle extending through an opening in a retraction plate 756 held against the front wall of the hub by a locking and releasing mechanism 780. An operating spring 754 is disposed concentrically around the needle and connected between the retraction plate 756 and the operating flange 748 to bias the needle distally to an extended position with the trailing edge 744 disposed beyond the distal end 792 of the cannula 734. A retracting spring 760 is connected between the retraction plate 756 and the rear wall of the hub and, if desired, a guide rod 761 can be provided to ensure axial alignment of the spring 760. A locking and releasing mechanism 780 similar to the locking and releasing mechanism 280 of FIG. 12 is disposed in the hub 736 to actuate the retraction mechanism.

Use of the automatic retractable safety penetrating instrument 730 is similar to that described for the instrument 530 of FIG. 17. When the automatic retractable safety penetrating instrument 730 is forced against tissue forming a cavity wall, the force from tissue contact will cause the safety probe 765 to move proximally against the bias of the spring 779 to expose the sharp tip 740 of the needle 732. Similarly, the force from tissue contact will cause the needle 732 to move proximally against the bias of the operating spring 754 until the trailing edge 744 is aligned with the distal end 792 of the cannula and the instrument is in an operative state for penetrating a cavity wall. Various types of stop members can be provided to limit proximal movement of the needle and the safety probe. With the instrument 730 in the operative state to penetrate tissue, the trailing edge 744 will be aligned with the cannula distal end 792 and the safety probe 765 will be disposed within the open distal end of the needle to expose the sharp tip 740. Once penetration into the anatomical cavity is completed, the safety probe 765 will automatically be moved distally due to the bias of the spring 779 such that the safety probe is returned to the extended, normally protruding position. The needle 732 will also be moved distally due to the bias of the operating spring 754 such that the operating flange 748 will engage the trigger cam 788 causing the leg 791 to bend or flex the arm 784 downwardly looking at FIG. 19 disengaging the locking member 786 from the retraction plate 756. The retracting spring 760 will automatically cause the retraction plate 756 to be moved proximally carrying with it the needle 732, as shown in FIG. 20, such that the sharp tip 740 of the needle is disposed within the cannula 734 while the safety probe 765 remains in the extended position. The instrument 730 is particularly useful in creating or forming a space in an anatomical cavity between a layer of tissue within the cavity and the cavity wall in that the blunt distal end of the safety probe moves tissue away from the cavity wall maintaining a space between the tissue and the wall with the size of the space corresponding to the distance that the safety probe protrudes into the cavity. The safety probe and needle can be arranged such that the distance that the safety probe protrudes following retraction can be controlled in accordance with the size of a potential space to be created in the anatomical cavity. Irrigation and aspiration procedures can be performed through the safety probe wherein an aperture is provided at the distal end thereof. The safety probe can be removed from the needle leaving the needle in place or the safety probe and needle can be withdrawn from the cannula leaving the cannula in place in the cavity.

FIG. 21 illustrates another modification of an automatic retractable safety penetrating instrument 830 according to the present invention. The automatic retractable safety penetrating instrument 830 includes a cannula 834 having a proximal end mounted in or formed as part of the hub 836, a needle 832 disposed within the cannula and a safety shield 833 concentrically disposed between the needle and the cannula. The needle terminates proximally at a flange 856 serving as a retraction plate disposed within the hub, and the tube 850 extends distally through a rear wall of the hub and through an opening in the retraction plate 856 into the hollow proximal end of the needle. An annular rim 879 is formed on an end of the tube 850 disposed within the proximal end of the needle, and a retracting spring 860 is disposed concentrically around the tube 850 and connected between the rim 877 and the retraction plate 856 to bias the needle to a retracted position with the sharp tip 840 of the needle within the cannula. The retraction plate 856 is held by a locking and releasing mechanism 880 to position the needle in an operative state with the trailing edge 844 substantially aligned with the distal end 892 of the cannula. The locking and releasing mechanism 880 includes at least one latch or locking spring having a substantially flat base 882 secured to a wall of hub 836 with an arm 884 bent inwardly therefrom to extend in the direction of the longitudinal axis of the instrument. A bent locking finger or member 886 is carried on a distal end of the arm 884 to engage the retraction plate 856 to prevent movement thereof when the locking spring is in its normal position as illustrated in FIG. 21. An extension 887 extends distally from the locking member 886 substantially parallel with the instrument axis, and a releasing or trigger member 888 extends rearwardly or proximally from extension 887 at an angle to allow movement of operating flange 848 thereby in a proximal direction without causing bending of arm 884. The safety shield 833 has a distal peripheral edge 835 and a proximal end terminating at an operating member or flange 848 disposed within the hub. An operating spring 854 is mounted concentrically around the safety shield and connected between the front wall of the hub 836 and the operating flange 848 to bias the safety shield to an extended position with the peripheral edge 835 normally protruding beyond the sharp tip 840 of the needle in the operative state. The safety shield 833 is movable proximally against the bias of the operating spring 854 during penetration of tissue until the operating flange 848 abuts the retraction plate 856, the retraction plate serving as a positive stop limiting proximal movement of the safety shield. Upon penetration into an anatomical cavity the safety shield 833 is movable distally due to the bias of the operating spring 854 to engage the trigger member 888 disposed distally of the retraction plate 856 a distance corresponding to the amount of distal movement desired for the safety shield prior to retraction. One or more locking springs can be provided and, as shown, two locking springs are provided at diametrically opposed locations with the needle.

The automatic retractable safety penetrating instrument 830 is used in a manner similar to that described above for the automatic retractable safety penetrating instrument of FIG. 19. As the automatic retractable safety penetrating instrument 830 is forced against tissue of a cavity wall, the proximal force from tissue contact will cause the safety shield 833 to move distally against the bias of the operating spring 854 until the operating flange 848 abuts the retraction plate 856, and the distal peripheral edge 835 of the safety shield 833 will be substantially aligned with the distal end 892 of the cannula 834 such that the sharp tip 840 of the needle 832 is exposed. Upon penetration into the anatomical cavity, the safety shield 833 will be moved distally due to the bias of the operating spring 854 such that the operating member 848 engages the trigger members 888 and flexes the arms 884 in a direction outwardly from the longitudinal axis of the instrument looking at FIG. 21 to disengage the locking members 886 from the retraction plate 856. With the retraction plate 856 disengaged from the locking members 886, the needle 832 will automatically be moved proximally to a retracted position due to the bias of the retracting spring 160 with the sharp tip 840 of the needle disposed within the cannula 834 while the safety shield 833 remains extended.

FIGS. 22, 23 and 24 show various modifications of distal tip configurations for the penetrating member of the automatic retractable safety penetrating instruments of the present invention. In FIG. 22, the penetrating member 932 is shown as a needle having an open distal end 938 including an acutely angled distal end surface 942 with a portion of the distal end curving toward the longitudinal axis of the needle 932 to terminate at a sharp tip 940 laterally or radially disposed from the wall of the needle. The distal end configuration of FIG. 22 is particularly advantageous for insertion into a wall of an anatomical cavity with a spoon-like, scooping or curving motion. FIG. 23 shows the distal end 938' of the penetrating member 932' as being formed of a plurality of solid, flat surfaces or facets 942' terminating distally at the sharp tip 940', and the facets can have a pyramidal or any other geometric configuration. FIG. 24 shows the distal end 938" of the penetrating member 932" as being formed as a cone terminating distally at the sharp tip 940", and a helical thread 931" is disposed along the cone allowing the penetrating member 930" to penetrate tissue with a slow, rotational motion such that gradual advancement of the penetrating member allows even very small or narrow anatomical cavities to be safely penetrated.

Automatic retractable safety penetrating instruments according to the present invention can incorporate various features of the modifications and embodiments disclosed herein and in applicant's co-pending patent applications referenced hereinabove, the specifications of which are incorporated herein by reference, dependent upon specific procedures to be performed. For example, the penetrating member can be solid or hollow and have distal ends of various configurations, such as open, needle-like configurations, multi-faceted, conical and threaded configurations. The positions of the retracting and operating springs can be coaxial, concentric, laterally offset, within the penetrating member or external of the penetrating member dependent upon size constraints for the hub associated with specific uses for the instruments. Where the springs are laterally offset, the hub can have a reduced length; and, where the springs are aligned with the longitudinal axis of the instrument, the hub can have a reduced width. When the springs are concentrically disposed and positioned within the penetrating member, the overall size of the hub can be minimized. The springs can be loaded or biased in either tension or compression; and, preferably, the instruments are supplied for use with the springs in relaxed or unloaded states to increase shelf life. The pin and slot arrangement between the penetrating member and the hub provides the surgeon with control over the instrument to allow use without retraction and to allow manual movement of the penetrating member to an operative position with the distal end of the penetrating member extending from the distal end of the outer sleeve and in alignment therewith to have the appearance of a standard penetrating instrument. The pin and slot arrangement as well as various other arrangements, such as threads and lugs, provides control over distal movement of the penetrating member to various extended positions following retraction. Movement of the pin also produces a visual indication of retracting and extending operation of the instrument which can also be determined by feel and sound both upon movement to the locked extended position and to the retracted position as well as visually by an observable color change through a transparent portion of the hub.

The hub arrangement used in the automatic retractable safety penetrating instruments will depend upon procedural requirements and the springs and locking or releasing mechanisms housed therein. The hub can be provided with or without a valve, and can be coupled with or formed as part of various devices, such as syringes, bags and bottles, for aspiration and irrigation. A guide tube can be used to extend from the hub rear wall into the hollow proximal end of the penetrating member or the safety probe to provide a fluid passage through the instrument as well as a passage for receiving other instruments, such as lasers. A detection device utilizing a floating ball can be mounted in communication with the lumen of the instrument to provide a visual indication of fluid flow through the instrument. The hub can be designed with the rear wall or a portion thereof removable allowing the penetrating member to be removed from the outer sleeve. Where a safety probe is disposed within the penetrating member, the safety probe alone can be withdrawn from the penetrating member leaving the penetrating member in place or both the safety probe and the penetrating member can be withdrawn from the outer sleeve. Where a safety shield is disposed between the penetrating member and the outer sleeve, the penetrating member alone can be withdrawn from the safety shield, or both the safety shield and the penetrating member can be withdrawn from the outer sleeve. Where safety probes or safety shields are utilized, the safety probes and safety shields can be arranged to remain in an extended position within an anatomical cavity even while the penetrating member is retracted to a safe, protected position.

Various arrangements can be utilized to allow the penetrating member to be manually moved to extended positions protruding from the distal end of the outer sleeve and into an anatomical cavity following retraction of the penetrating member. Where a pin and slot arrangement is utilized, various intermediate transverse slot portions can be provided allowing the penetrating member to be locked in place at various intermediate extended positions. Extension of the penetrating member within an anatomical cavity following retraction can be accomplished with gradual advancement of the penetrating member via the pin and slot arrangement, as well as the use of threads or lugs coupling the penetrating member with the tube, and various other devices can be used to selectively, controllably extend the penetrating member following retraction.

Various arrangements can be utilized to stabilize, anchor or hold the automatic retractable safety penetrating instrument within an anatomical cavity selectively or automatically with retraction upon the instrument entering the cavity. The outer sleeve can be provided with various expandable, distensible, or shape changing devices movable to positions bent, offset or outwardly of the longitudinal axis of the instrument to stabilize the instrument within the anatomical cavity and prevent withdrawal therefrom.

The automatic retractable safety penetrating instrument can have parts thereof, such as the knob or the tube, connected with a source of electric current to transmit current along a component, such as the penetrating member, of the instrument to perform electrosurgical procedures within the cavity. By forming the component of electrically conductive material and other exposed parts of the instrument of insulative material, the automatic retractable safety penetrating instrument allows electrosurgical procedures to be performed with greater precision, control and safety.

The locking and releasing mechanism chosen for the automatic retractable safety penetrating instruments will depend on ease of manufacture and assembly, holding or locking forces required and releasing forces required. The spacing of the trigger from the operating member during tissue penetration will determine the distal movement required of the operating member prior to automatic retraction. The configuration of the trigger will depend on the bias force on the operating member and the amount of movement required of the locking member to release the retraction member. Resilient, elastic, rubber or sponge members can be used as bias devices, and the resilient, elastic, rubber or sponge members can be formed to define a stop or abutment limiting proximal movement of the operating member to assure alignment at a distal end of the instrument.

Automatic retractable safety penetrating instruments according to the present invention can be formed of two, three or more cylindrical or tubular members, and the members can be flexible, rigid, semi-rigid as well as transparent, opaque or radio-opaque.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A method of performing surgical procedures comprising the steps of
   penetrating tissue with a sharp tip of a penetrating member disposed within a cannula to position a distal end of the cannula in the tissue;
   automatically retracting the sharp penetrating member tip within the cannula in response to desired positioning of the cannula in the tissue;
   moving the penetrating member distally within the cannula with the cannula distal end positioned in the tissue to cause the sharp penetrating member tip to protrude beyond the cannula distal end; and
   performing a procedural step using the penetrating member.

2. A method as recited in claim 1 wherein the penetrating member is hollow and said performing step includes fluid aspiration through the penetrating member.

3. A method as recited in claim 1 wherein the penetrating member is hollow and said performing step includes fluid infusion through the penetrating member.

4. A method as recited in claim 1 and further comprising the step of completely withdrawing the penetrating member from the cannula.

5. A method as recited in claim 1 wherein the penetrating member includes a proximal end mounted in a hub and a pin disposed on the penetrating member received in a slot in the hub and said step of moving includes moving the pin along the slot.

6. A method of performing surgical procedures comprising the steps of
   penetrating an anatomical cavity with a sharp tip of a penetrating member disposed within a cannula to position the cannula in the anatomical cavity;
   retracting the sharp tip of the penetrating member within the cannula automatically upon positioning of the cannula in the anatomical cavity;
   automatically stabilizing the cannula within the anatomical cavity in response to automatic retraction of the penetrating member; and
   performing a procedural step through the cannula.

7. The method as recited in claim 6 wherein the penetrating member is hollow and said step of performing includes performing a procedural step through the penetrating member.

8. A method as recited in claim 6 wherein said performing step includes fluid aspiration through the penetrating member.

9. A method as recited in claim 6 wherein said performing step includes fluid infusion through the penetrating member.

10. A method as recited in claim 6 further including the step of completely withdrawing the penetrating member from the cannula and said step of performing includes performing a procedural step through the cannula.

11. A method as recited in claim 6 wherein said step of stabilizing includes changing the shape of the cannula within the anatomical cavity.

12. A method of performing surgical procedures comprising the steps of
    penetrating tissue with a sharp tip of a penetrating member disposed within a cannula to position a distal end of the cannula in the tissue;
    automatically retracting the sharp penetrating member tip within the cannula in response to desired positioning of the cannula in the tissue;
    moving the penetrating member distally to cause the sharp penetrating member tip to protrude beyond the cannula distal end; and
    performing a procedural step using the penetrating member, said performing step including cauterizing tissue using the penetrating member.

13. A method as recited in claim 12 wherein the penetrating member is tubular and said performing step includes injecting fluid through the penetrating member after said cauterizing step.

14. A method as recited in claim 12 wherein said cauterizing step includes electric coagulation.

15. A method as recited in claim 12 wherein said cauterizing step includes electric cutting.

16. A method of performing surgical procedures comprising the steps of
    penetrating tissue with a sharp tip of a hollow penetrating member disposed within a cannula to position a distal end of the cannula in the tissue;
    automatically retracting the sharp penetrating member tip within the cannula in response to desired positioning of the cannula in the tissue;
    moving the penetrating member distally to cause the sharp penetrating member tip to protrude beyond the cannula distal end; and
    performing a procedural step using the penetrating member, said performing step including inserting instruments through the penetrating member.

17. A method as recited in claim 16 wherein said performing step includes inserting a laser through the penetrating member.

18. A method of performing surgical procedures comprising the steps of
    penetrating tissue with a sharp tip of a penetrating member disposed within a cannula to position a distal end of the cannula in the tissue, said penetrating member having a proximal end mounted in a hub and a tube extending through the hub and into the proximal end of the penetrating member;
    automatically retracting the sharp penetrating member tip within the cannula in response to desired positioning of the cannula in the tissue;
    moving the penetrating member distally to cause the sharp penetrating member tip to protrude beyond the cannula distal end, said moving step including moving the penetrating member with an end of the tube disposed externally of the hub; and
    performing a procedural step using the penetrating member.

19. A method as recited in claim 18 further including, prior to said moving step, coupling the tube with the penetrating member.

20. A method as recited in claim 19 wherein the proximal end of the penetrating member has an internal thread and the tube carries an external thread and said step of coupling includes engaging the thread on the tube with the thread on the penetrating member.

21. A method as recited in claim 19 wherein the penetrating member proximal end includes a flange having slots disposed around the tube and the tube includes lugs within the penetrating member and alignable with the slots to withdraw the lugs from the penetrating member and said step of coupling includes aligning the lugs with the slots to withdraw the lugs from the penetrating member and moving the lugs out of alignment with the slots to position the lugs against the flange.

22. A method of performing surgical procedures comprising the steps of penetrating an anatomical cavity with a sharp tip of a penetrating member disposed within a cannula to position the cannula in the anatomical cavity;

retracting the sharp tip of the penetrating member within the cannula upon positioning of the cannula in the anatomical cavity;

automatically stabilizing the cannula within the anatomical cavity in response to retraction of the penetrating member;

completely withdrawing the penetrating member from the cannula;

performing a procedural step through the cannula, said step of performing including inserting an instrument for performing a lumpectomy through the cannula.

* * * * *